United States Patent
Höök et al.

(10) Patent No.: US 6,413,931 B1
(45) Date of Patent: Jul. 2, 2002

(54) PEPTIDE INHIBITOR OF FIBRINOGEN BLOOD CLOTTING

(75) Inventors: Magnus A. Höök, Houston, TX (US); Vivian W-C Yang, Taipei (TW)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/567,912

(22) Filed: May 10, 2000

Related U.S. Application Data

(60) Provisional application No. 60/133,327, filed on May 10, 1999.

(51) Int. Cl.⁷ ........................ A01N 61/00; A61K 31/00; G01N 33/53
(52) U.S. Cl. ........................ 514/2; 435/7.1; 435/810; 435/217; 514/822
(58) Field of Search ................ 514/2, 822, 53, 514/54; 435/810, 7.1, 217; 436/11, 149

(56) References Cited

U.S. PATENT DOCUMENTS 5,650,389 A  7/1997  Krumdieck et al.

FOREIGN PATENT DOCUMENTS

EP  0 671 414 A  9/1995

OTHER PUBLICATIONS

Merle et al., J of Cellular Biochemistry, 75: 538–546. Decorin inhibits cell migration through a process requiring its glycosaminoglycan side chain, Dec. 1, 1999.*
Delorme et al., Thromb. Res. (1998), 90(4): 147–153. Anticoagulant dermatan sulfate proteoglycan (Decorin) in the term human placenta.*
Spence et al., Human Anatomy & Physiology, Third edition, (1987). The Benjamin/Cummings Publishing Co., Inc., USA. Chapter 17: The Circulatory System, pp. 505–525.*
Levoeuf, R. D. et al., "Effects of Hyaluronic Acid and Other Glycosaminoglycans on Fibrin Polymer Formation", Biochemistry, 1987, 26, 6052–6057.
Yang, Vivian W–C, et al., "Decorin is a $Zn^{2+}$ Metalloprotein", Journal of Biological Chemistry, 1999, 274, 12454–12460.
International Search Report, PCT, Nov. 30, 2000.
Brister, S. J., Ofosu, F. A., Heigenhauser, G. J., Gianese, F., and Buchanan, M. R. "Is Heparin the Ideal Anticoagulant for Cardiopulmonary Bypass? Dermatan Sulphate May Be an Alternate Choice", (1994) Thromb. Haemost. 71(4), 468–473.
Lacoviello, L., D'Adamo, M. C., Pawlak, K., Polishchuck, R., Wollny, T., Buczko, W., Donati, M. B. "Antithrombotic Activity of Dermatan Sulphates, Heparins and their Combination in an Animal Model of Arterial Thrombosis", (1996) Thromb. Haemost. 76(6), 1102–1107.
Laudano, A. P. and Doolittle, R. F. "Synthetic peptide derivatives that bind to fibrinogen and prevent the polymerization of fibrin monomers", (1978) Proc. Natl. Acad. Sci. 75, 3085–3089.
Linhardt, R. J., Desai, U. R., Liu, J., Pervin, A., Hoppensteadt, D., and Fareed, J. "Low Molecular Weight dermatan Sulfate As An Antithrombotic Agent—Structure–Activity Relationship Studies", (1994) Biochem. Pharmacol. 47(7), 1241–1252.
Pratt, K. P., Côté, H. C. F., Chung, D. W., Stenkamp, R. E., and Davie, E. W. "The primary fibrin polymerization pocket: Three–dimensional structure of a 30–kD C–terminal γ chain fragment complexed with the peptide Gly–Arg–Pro", (1997) Proc. Natl. Acad Sci. 94, 7176–7181.
Schmidt, G., Hausser, H., and Kresse, H. "Interaction of the small proteoglycan decorin with fibronectin—Involvement of the sequence NKISK of the core protein", (1991) Biochem J. 280, 411–414.
Schmidt, G., Robenet, H., Harrach, B., Glossl, J., Nolte, V., Hormann, H., Richter, H., and Kresse, H. "Interaction of Small Dermatan Sulfate Proteoglycan from Fibroblasts with Fibronectin", (1987) J. Cell Biol. 104, 1683–1691.
Whinna, H. C., Choi, H. U., Rosenberg, L. C., and Church, F. C. "Interaction of Heparin Cofactor II with Biglycan and Decorin", (1993) J. Biol. Chem. 268, 3920–3924.

\* cited by examiner

*Primary Examiner*—Christopher R. Tate
*Assistant Examiner*—Michele C. Flood
(74) *Attorney, Agent, or Firm*—Howrey Simon Arnold & White, LLP

(57) ABSTRACT

A method of inhibiting fibrin clot formation is provided. The decorin protein, peptide, or related fragments are found to bind fibrinogen in the presence of Zinc ($Zn^{2+}$), thus preventing the formation of fibrin clots. The decorin protein, peptide, or related fragments can be utilized as an anticoagulant and in methods of preventing and/or treating diseases and disorders characterized by clot formation.

23 Claims, 8 Drawing Sheets

PEPTIDE INHIBITOR OF FIBRINOGEN BLOOD CLOTTING

This applications is based on U.S. Provisional Application No. 60/133,327, filed May 10, 1999, the entire contents of which are incorporated by reference herein.

BACKGROUND OF THE INVENTION

1. Field of the Invention

The present invention relates generally to the field of biology. More particularly, it concerns methods for inhibiting fibrin clot formation and the use of decorin, or related peptides as anticoagulating agents.

SLRPs encompass a class of secreted proteoglycans that include five structurally related but genetically distinct members: decorin, biglycan, fibomodulin, lumincan, and epiphycan, which was originally called PG-Lb. These proteoglycans share the unique feature of being composed primarily of leucine-rich tandem repeats that confer most of the biological functions. A close examination of the overall protein core structure reveals that it consists of three main regions: an amino-terminal region, which contains the negatively charged GAGs or tyrosine sulfate; a central domain with varying numbers of LRRs; and a carboxyl end region of poorly defined function. In all cases, the central domain is flanked by cysteine-rich clusters. In decorin, biglycan, and epiphycan, the amino-terminal region harbors 1–2 GAG chains that can be either dermatan or chondroitin sulfate.

2. Description of Related Art

Decorin is composed of a 40 kD core protein and usually carries a chondroitin sulfate/dermatan sulfate glycosaminoglycan (GAG) chain. Many GAGs effect blood coagulation activity. For example, heparin, and heparan sulfate (HS) have been used as efficient anticoagulants clinically for decades. Dermatan sulfate (DS) is also a potent anticoagulant both in vivo and in vitro (Brister, 1994; Linhardt, 1994; Lacoviello, 1996). However, the anticoagulation mechanisms of heparin/HS and DS are different. Heparin and HS both accelerate the activity of antithrombin III as it inhibits the activity of thrombin. Dermatan sulfate GAG, on the other hand, accelerates the inhibition activity of heparin cofactor II to thrombin (Tollefsen, 1983; Maimone, 1990). Antithrombin III and heparin cofactor II are inhibitors of serine proteases that inhibit blood coagulation by inhibiting the activity of thrombin and related serine proteases. Dermatan sulfate GAG isolated from decorin has anticoagulant activity, enhancing the inhibitory activity of heparin cofactor II to thrombin (Whinna, 1993). In contrast, both hyaluronic acid (HA) and chondroitin (CS) bind to the plasma protein fibrinogen and induce fibrin polymerization, resulting in decreased clotting time (LeBoeuf, 1987). The traditional anticoagulant heparin and the recent dermatan sulfate GAGs have been used in treating the patients and animals with thrombosis (Brister, 1994; Linhardt, 1994; Lacoviello, 1996). However, the side effect of hemorrhage has been a problem (Matthiasson, 1995).

Decorin is distributed in a variety of tissues such as skin, bone, cartilage, tendon, cornea, and blood vessel (lozzo, 1996). Decorin interacts with a variety of extracellular matrix (ECM) molecules such as collagens, fibronectin, and transforming growth factor β and regulates their biological functions in matrix assembly, cell adhesions, and signaling for cell proliferation and differentiation. These interactions are believed to be important in embryonic development, wound healing processes, as well as in pathogenic conditions such as atherosclerosis and tumorgenesis.

Decorin gene knock out mice have an abnormal arrangement of collagen fibrils which results in fragile skin (Danielson, 1997). In addition, decorin binds to several collagens, for example, type I, II, III, V, VI, and XIV through core protein or GAG chains, as shown in vitro binding studies (Pogany, 1992; Hedbom, 1993; Ramamurthy, 1996; Bidanset, 1992; Font, 1996; Font, 1993). Decorin associates with collagen fibers and regulates collagen fibrillogenesis (Rada, 1993; Brown, 1989, Vogel, 1984). The binding of decorin to collagen type I is mediated by the decorin core protein (Schönherr, 1995; Svensson, 1995; Dresse, 1997). Molecular modeling predicts that the ten LRRs of decorin core protein form a horse shoe like structure that accommodates a single type I collagen triple helix (Weber, 1996). Both in vitro and in vivo studies suggest that decorin is important in regulating the arrangement of collagen fibrils involved in matrix assembly.

Decorin interacts with other ECM molecules. For example, decorin binds to fibronectin with high affinity via its core protein (Schmidt, 1987; Schmidt, 1991). The interaction of decorin to fibronectin is affected in cell adhesion (Lewandowska, 1987; Bidanset, 1992). Soluble molecules in the ECM, such as a variety of growth factors, ions, and water, are important in cell signaling, controlling cell growth, and programming cell death. Decorin binds transforming growth factor β (TGFβ) and regulates its function in cell proliferation and differentiation (Hildebrand, 1994; Yamaguchi, 1990). Expression of decorin in colon carcinoma cells may inhibit cell growth by regulating the epidermal growth factor (EGF) signaling pathway (Moscatello, 1998; Patel, 1998). Additionally, decorin may bind to human complement C1q and inhibit activity of the C1 complex involved in inflammatory cascade (Krumdieck, 1992).

Zinc, a divalent cation ($Zn^{2+}$), plays important biological roles in the catalytic activity of enzymes and in the stabilization of protein structures. For example, metalloproteases require zinc ions to be active. Also, the zinc finger containing transcription factor complexes $Zn^{2+}$ to form a structure suitable to bind with DNA. The N-terminal cysteine containing domain of decorin binds $Zn^{2+}$ ions with high affinity, $K_D=3\times10^{-7}$ M, suggesting that $Zn^{2+}$ will interact with decorin in vivo (Yang, 1999). In addition, circular dichroism experiments indicate that $Zn^{2+}$ ions alter the secondary structure of the recombinant decorin N-terminal peptide (Yang, 1999). However, the function of decorin-$Zn^{2+}$ complex is unclear.

BRIEF DESCRIPTION OF THE DRAWINGS

The following drawings form part of the present specification and are included to further illustrate certain aspects of the invention. The invention can be better understood by reference to one of more of the drawings in combination with the detailed description of the specific embodiments presented herein.

SUMMARY OF THE INVENTION

Figure 1A:
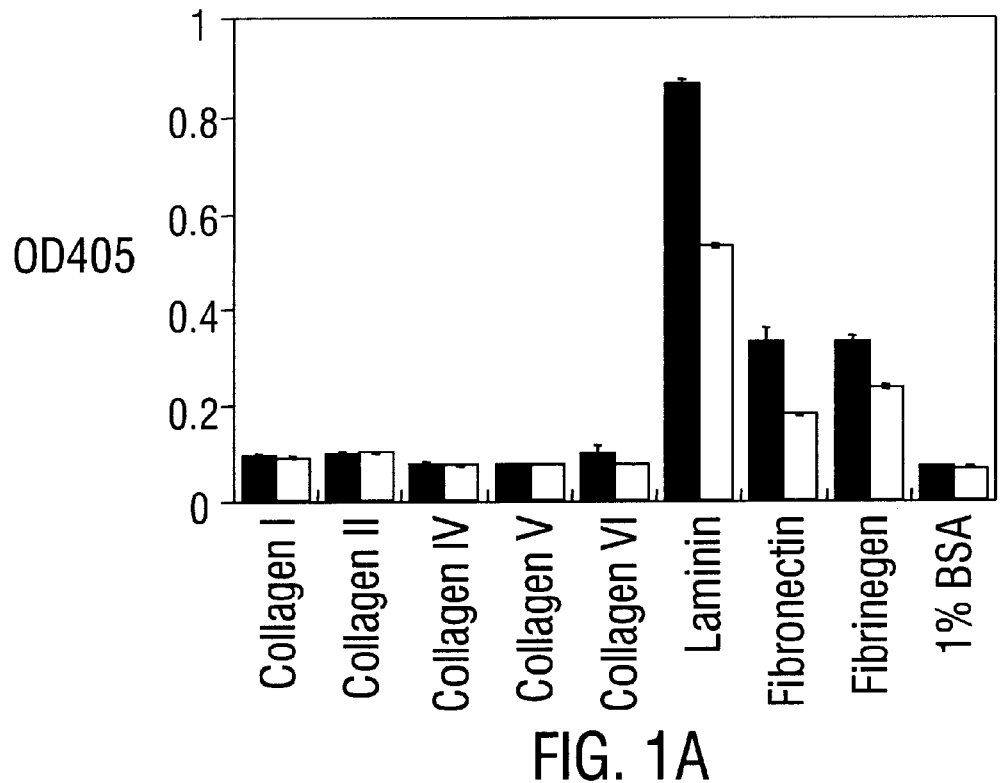
FIG. 1 Binding of decorin to ECM molecules in the presence or absence of $Zn^{2+}$ ions. Biotin-labeled recombinant intact decorin proteoglycan expressed by a vaccinia virus vector in eukaryotic cells (vvHDCN) (A) or recombinant decorin N-terminal core protein made as maltose binding protein fusion (MBP-MD4) (B) were tested to determine their binding activity to a series of ECM molecules coated on 96 microliter well plates washed with 20 mM Tris-HCl, 500 mM NaCl, pH 7.5 containing 0.5% tween-20. The black bar indicates that the binding assays were done in the presence of 5 mM $ZnCl_2$ and 1 mM EDTA in the buffer, the clear bar indicates that the binding assays were done in the presence of 1 mM EDTA in the buffer.

The present invention provides several novel methods and related biological compositions involved in the inhibition of fibrin clot formation. Also provided are methods of identifying substances that alter or modulate the interaction of various decorin protein fragment compositions with fibrinogen, and the substances so identified.

The invention first provides a method of inhibiting fibrin clot formation, comprising contacting fibrinogen with an amount of a decorin protein, fragment or related peptide composition effective to inhibit thrombin induced transformation of fibrinogen to fibrin, thus inhibiting coagulation.

As used herein, the term "inhibiting clot formation" will be understood to encompass any reduction in the time of clot formation or extent of clot formation when compared to control conditions in the absence of a decorin protein fragment composition. Thus, if the extent of clot formation or the time to achieve clot formation is taken to be 100% in the control condition in the absence of a decorin protein fragment composition, any reduction in the extent of clot formation or time to achieve clot formation will be understood to be beneficial. Thus substantial inhibition or prevention of the time or extent of clot formation is within the scope of the present invention, as exemplified by clot formation times or extents of about 99%, about 98%, about 97%, about 95%, about 90%, about 80%, about 75%, about 70%, about 60%, about 50%, about 40%, about 30%, about 25%, about 20%, about 15%, about 10%, about 5%, about 3%, about 1% or even the complete lack of, or prevention of, clot formation, in the presence of a decorin protein fragment composition. Intermediate values to those listed above are also within the scope of the invention.

In certain aspects of the invention, the decorin protein, fragment or related peptide composition is dispersed in a pharmaceutically-acceptable carrier. In other aspects of the invention, the fibrinogen to be contacted is comprised within an animal, and the decorin protein fragment composition is administered to the animal. In a particular aspect of the invention, the animal is a human subject.

The invention further provides a method of inhibiting fibrinogen aggregation, comprising contacting fibrinogen with an amount of a fibrinogen-binding decorin protein, fragment or related peptide composition effective to inhibit fibrinogen aggregation.

The invention also provides a method of inhibiting fibrin clot formation in a blood sample, the method comprising contacting the blood sample with an amount of a decorin protein, fragment or related peptide composition effective to inhibit fibrin clot formation in the sample.

In another embodiment of the invention, the decorin protein fragment composition is dispersed in a pharmaceutically-acceptable carrier. In an additional aspect of the invention, the blood sample is contained within an animal, and the decorin protein, fragment or related peptide composition is administered to the animal. In a further aspect of the invention, the animal is a human subject.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

The preferred dose for human administration will be determined based on the needs of the individual patient and the nature of the disorder being treated. Based on the preferred dose range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl(2-mercaptobenzoate-S)mercury sodium salt) (Sigma Chemical Company, St. Louis, Mo.).

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

The invention additionally provides a method of inhibiting fibrin clot formation in an animal, comprising providing to an animal an amount of a decorin peptide, fragment or related peptide pharmaceutical composition effective to inhibit fibrin clot formation in the animal. In certain aspects, the invention provides a method of inhibiting fibrin clot formation in an animal, comprising providing to an animal an amount of a fibrinogen binding decorin protein, fragment or related peptide pharmaceutical composition effective to bind to fibrinogen and inhibit fibrin clot formation in the animal.

In a particular embodiment of the invention, the decorin protein, fragment or related peptide binds to or interacts with fibrinogen. In a further embodiment of the invention, the decorin protein, fragment or related peptide binds to or interacts with the -subunit of fibrinogen. In a still further embodiment of the invention, the decorin protein or peptide binds to or interacts with a subunit of fibrinogen.

The invention also provides a kit for inhibiting fibrin clot formation comprising, in suitable container means, a decorin peptide fragment composition and at least a first distinct anti-coagulating compound.

Also provided is a method for identifying a candidate substance that alters the binding of a decorin protein, fragment or related peptide to fibrinogen, that may be characterized as comprising the steps of admixing a composition comprising a decorin protein, fragment or related peptide with a fibrinogen preparation and a candidate substance, and determining the ability of the decorin protein, fragment or related peptide to bind to the fibrinogen preparation in the presence and in the absence of the candidate substance, wherein the ability of the candidate substance to alter the binding of the decorin protein, fragment or related peptide to the fibrinogen preparation is indicative of a candidate substance that alters the binding of a decorin protein or peptide fragment to fibrinogen. In a further aspect of the invention, the decorin protein or peptide fragment is prepared by recombinant means.

In a particular embodiment of the invention, the method is further defined as a method for identifying a candidate substance that promotes the binding of a decorin protein, fragment or related peptide to fibrinogen, comprising determining the ability of a candidate substance to increase the binding of a decorin protein, fragment or related peptide to fibrinogen upon admixing with a composition that comprises a decorin protein, fragment or related peptide. In another aspect of the invention, the method is further defined as a method for identifying a candidate substance that inhibits the binding of a decorin protein, fragment or related peptide to fibrinogen, comprising determining the ability of a candidate substance to decrease the binding of a decorin protein, fragment or related peptide to fibrinogen upon admixing with a composition that comprises a decorin protein, fragment or related peptide and a fibrinogen preparation.

Further provided is a modulator of decorin protein or peptide fragment binding to fibrinogen, prepared by a process comprising the steps of admixing a composition comprising a decorin protein or peptide fragment with a fibrinogen preparation and a candidate modulator, identifying a modulator that alters the binding of the decorin protein or peptide fragment to fibrinogen by determining the ability of the decorin protein or peptide to bind to the fibrinogen preparation in the presence and in the absence of the candidate modulator, wherein the ability of the candidate modulator to alter the binding of the decorin protein or peptide fragment to the fibrinogen preparation is indicative of a candidate modulator that alters the binding of a decorin protein or peptide fragment to fibrinogen, and obtaining the modulator so identified.

Thus, the invention also provides a method of modulating decorin protein or peptide fragment binding to fibrinogen, comprising contacting a composition comprising fibrinogen and a decorin protein or deocorin peptide fragment with an effective amount of a substance that modulates decorin protein or peptide fragment binding to fibrinogen. In one aspect of the invention, the method may be further defined as a method for promoting the binding of a decorin protein or peptide fragment to fibrinogen, comprising contacting the composition with an effective amount of a substance that increases the binding of a decorin protein or peptide fragment to fibrinogen. In another aspect of the invention, the method may be further defined as a method for inhibiting the binding of a decorin protein or peptide fragment to fibrinogen, comprising contacting the composition with an effective amount of a substance that decreases the binding of a decorin protein or peptide fragment to fibrinogen.

In a particular embodiment of the invention, the composition is comprised within an animal. In an additional embodiment of the invention, the animal is a human subject.

The invention also provides a method for identifying a candidate decorin peptide fragment with improved fibrinogen binding, that may be characterized as comprising the steps of admixing a composition comprising a candidate decorin peptide fragment with a fibrinogen preparation, and determining the ability of the candidate decorin peptide fragment to bind to the fibrinogen preparation, wherein a candidate decorin peptide fragment that exhibits improved binding to fibrinogen as compared to wild-type decorin is indicative of a candidate decorin peptide fragment with improved fibrinogen binding.

When labeled with a detectable biomolecule or chemical, the decorin protein or peptide fragment described herein is useful for purposes such in vitro detection of fibrinogen in a sample. Laboratory research may also be facilitated through use of such protein-label conjugates. Various types of labels and methods of conjugating the labels to the proteins are well known to those skilled in the art. Several specific labels are set forth below. The labels are particularly useful when conjugated to a protein such as an antibody or receptor. For example, the protein can be conjugated to a radiolabel such as, but not restricted to, $^{32}P$, $^{3}H$, $^{14}C$, 35S, $^{125}I$, or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allophycocyanin, phycocyanin, rhodamine, and Texas Red. The fluorogens are generally detected by a fluorescence detector.

The protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol$^a$) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

Further, when administered as a pharmaceutical composition to a patient or used to coat medical devices or polymeric biomaterials in vitro and in vivo, decorin protein, fragment or related peptide prevents or inhibits fibrin clot formation at the wound site or around the biomaterials themselves. Medical devices or polymeric biomaterials to be coated with the decorin protein, fragment or related peptide described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the decorin protein, fragment, or related peptide to a surface of the device, preferably an outer surface that would be exposed to fibrinogen. The surface of the device need not be entirely covered by the decorin protein, fragment, or related peptide.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Applicants have found that N-terminal domain of decorin exhibits fibrinogen binding activity and inhibits the thrombin induced transformation of fibrinogen to fibrin, thus inhibiting blood coagulation. Zinc ions are required for decorin to bind with fibrinogen. The binding of decorin to fibrinogen is mediated by the decorin N-terminal domain, which coordinates with $Zn^{2+}$ ions to form a structure for fibrinogen binding. $Ni^{2+}$ and $Cd^{2+}$ can also enhance decorin binding affinity to fibrinogen. The physiological amount of $Zn^{2+}$ ions (15 uM) should be adequate to facilitate the interaction between decorin and fibrinogen.

Decorin N-terminal domain is a very strong inhibitor of clot formation. The blood anticoagulation activity of decorin or of the attached GAG chains on decorin may be important in specific tissues such as the placenta in pregnant females at delivery.

EXAMPLES

ECM Molecules

Collagen type I from rat tail was purchased from Collaborative Biomedical Products (Bedford, Mass.). Collagen Type II from bovine nasal septum was from Sigma (St. Louis, Mo.). Collagen type IV, V, and VI were purchased from Southern Biotechnology Associates (Birmingham, Ala.). Fibronectin was purified from human plasma as described by Vuento and Vaheri (Vuento, 1979). Human fibrinogen was purchased from Chromogenix (Sweden). Fibrinogen D and E fragment were purchased from Calbiochem (La Jolla, Calif.).

Preparation of Decorin and MD4 Peptides

The recombinant intact human decorin proteoglycan (vvHDCN) was produced by vaccinia virus expression system in eukaryotic cells. A series of decorin core protein fragments have been expressed as maltose binding protein (MBP) fusions. The MD4 peptide was isolated from a recombinant GST-MD4 fusion protein.

Reduction and Alkylation of MD4 Peptide

Lyopholized MD4 peptide were dissolved in 10 mM of dithiothreitol (DTT) for 1 h at about 25° C. and subsequently incubated with 10 mM iodoacetamide in 20 mM Tris-HCl pH 8.0 for another 1 h at about 25° C. The reduced and alkylated peptide was then purified by PD-10 desalting column (Pharmacia, Piscataway, N.J.) and stared at 20 mM Tris-HCl, 150 mM NaCl, pH 7.4 buffer.

Biotinylation of Decorin

Purified recombinant full length decorin proteoglycan (vvHDCN), full length decorin core protein and decorin N-terminus made as MBP fusion proteins, MBP-MD and MBP-MD4, respectively, and MBP were first dialyzed against PBS (8.4 mM $Na_2HPO_4$, 1.9 mM $NaH_2PO_4$, 150 mM NaCl pH 7.4) with three buffer changes. The protein was then concentrated to 2 mg/ml by using centricon-10 (Amicon, Beverly, Mass.) and incubated end-over-end with 75 ul of Sulfo-NHS-Biotin (1 mg/ml in water) (Pierce, Rockford, Ill.) at 4° C. for overnight. Subsequently, the labeled protein was dialyzed against 20 mM Tris-HCl, 150 mM NaCl, pH 7.5 at 4° C. with three buffer changes. The protein concentration was determined by the molar extinction coefficient ($\epsilon$), $\epsilon_{vvHDCN}$=19862, $\epsilon_{MBP-MD}$=92880, $\epsilon_{MBP-MD4}$=69080, or $\epsilon_{MBP}$32 65800 and absorbance at $A_{280}$.

Enzyme-linked Immunosorbent Binding Assay

Immulon-1 96 microtiter plate wells (Dynatech Labs, Chantilly, Va.) were coated with variant extracellular matrix molecules 1 ug/50 ul TBS (20 mM Tris-HCl, 500 mM NaCl, pH 7.5) per well by incubating at 4° C. for overnight. The remaining protein binding sites in the wells were blocked by incubating 1% BSA in TBS, 200 ul per well for 1 h. The wells were then washed with TBS containing 0.1% BSA and 0.5% Tween-20, 200 ul per well for 3 times, each time for 5 min at about 25° C. Subsequently, the biotin labeled decorin or MBP was added to the wells at final concentration $4 \times 10^{-8}$ M in 50 ul TBS with 0.1% BSA in the presence of 5 mM $ZnCl_2$ and 1 mM EDTA or 1 mM EDTA by incubating for another 1 h. The unbound protein was removed by triplicate decantings and washings with low or high TBST, each time for 5 min. The bound protein was labeled with streptavidin-alkaline phosphatase conjugate (Boehringer Mannheim, Germany), 100 ul per well at 1: 10000 (v/v) dilution in TBS with 0.1% BSA to allow interaction for 30 min. After three washes, the phosphatase linked bound protein could be detected by adding "Sigma 104" phosphate substrate (Sigma Diagnostic, St. Louis, Mo.) 1 mg/ml, 100 ul per well, in DEA buffer (1 M diethanolamine, pH 9.8, 0.5 mM $MgCl_2$) and incubating at 37° C. for 30 min. Any bound protein was developed as yellow color and the amount can be measured by reading absorbance at $A_{450}$.

Inhibition Binding Assay

The protocol was based on the enzyme-linked immunosorbant binding assay as described above. However, the inhibitors were mixed with biotin labeled protein and allowed to bind to coated molecules in microtiter wells and incubated for 1 h at room temperature.

Fluorescence-labeling of MD4 Peptide

MD4 peptide (2 mg/ml) in deionized water was incubated with fluorescein succinimidyl ester (20 mM) in DMSO at 5 to 1 molar ratio in coupling buffer (100 mM $KH_2PO_4$, pH 7.0) for about 60 min at about 37° C. The reaction was quenched by the addition of 10 ul, 1 M Tris-HCl pH 8.0 per 100 ul reaction, vortexed, and left at room temperature for another 30 min. The fluorescein labeled MD4 peptide was purified and changed buffer to 20 mM Tris-HCl, 150 mM NaCl, pH 7.5 by a PD-10 column (Pharmacia, Piscataway, N.J.).

Fluorescence Polarization

Fluoresceinated peptide (50 nM) was incubated with a series concentration of binding ligand (fibrinogen or fibrinogen D fragment) at room temperature for 3 h. The total volume of each reaction was 1 ml in 20 mM Tris-HCl, 150 mM NaCl, pH 7.5, supplement with 15 uM $ZnCl_2$ or 1 mM EDTA. The samples were then analyzed using a Beacon fluorescence polarization system. Binding curves were analyzed by nonlinear regression curve fitting program in KaleidaGraph (Synergy software, Reading, Pa.). The equation was defined as follows, $$\Delta P = \frac{\Delta P_{\max} \cdot [\text{protein}]}{K_D + [\text{protein}]}$$

P is the changes in fluorescence polarization, $P_{MAX}$ is the maximum changes in fluorescence polarization, and $K_D$ is the dissociation constant of the interaction. A single ligand-binding site was assumed in this analysis.

Western Ligand Blot Binding Assay

Three micrograms of human fibrinogen were loaded on a 10% SDS-PAGE to separate three polypeptide chains of fibrinogen. The protein bands on the polyacrylamide gel were then transferred to a immobilon-P transfer membrane (Millipore, Bedford, Mass.) by a semi-dry electroblot system (BioRad, Hercules, Calif.). To block any additional protein binding sites, 5% non-fat dried milk (w/v) in TBS was incubated with the membrane for 1 h at room temperature, followed by 3 washes with TBST, each wash for 5 min. The biotin-labeled MBP-MD4, 0.5 ug ml$^{-1}$ in TBS with 0.1% milk was then added to the membrane and incubated for 1 h at room temperature to allow the binding interaction. After 3 washes, streptavidin-alkaline phosphatase conjugate was added at 1:5000 ratio (v/v) in TBST with 0.1% milk and incubated with the membrane for 1 h at room temperature. The membrane was washed and the fibrinogen polypeptide chain which bound with MBP-MD4 was visualized by the p-nitroblue tetrazolium (NBT)/5-bromo4-chloro-3-indoyl phosphate p-toluidine salt (BCIP) reagent (BioRad, Hercules, Calif.). Stock solutions of NBT and BCIP were made according to the manufacture's instructions and diluted in carbonate bicarbonate buffer (14 mM $Na_2CO_3$, 36 mM $NaHCO_3$, 5 mM $MgCl_2.6H_2O$, pH 9.8) to a final concentration of 300 ug NBT and 150 ug BCIP ml$^{-1}$.

Clotting Assay

These tests were conducted by incubating 1 mg of human fibrinogen with desired peptides in 20 mM Tris-HCl, 150 mM NaCl, pH 7.5 in the presence or absence of $Zn^{2+}$ for at least 30 min followed by adding 1 unit of bovine thrombin. The total volume of each reaction was 1 ml and the reaction was observed by counting the time for allowing the solution to form a gel like clot in the test tube.

$Zn^{2+}$ Affect in the Binding of Decorin Proteoglycan to Extracellular Matrix Molecules Decorin binds to $Zn^{2+}$ ions mediated by the N-terminal domain of the core protein. The $Zn^{2+}$ ions complex with decorin N-terminal domain and modulate its secondary structure (Yang, 1999). To investigate the affect of $Zn^{2+}$ ions in decorin-ECM molecule interactions, solid phase binding assays were carried out to compare the binding activity of biotin-labeled recombinant intact decorin (vvHDCN) or N-terminal domain of decorin core protein (MBP-MD4) in the presence or absence of $Zn^{2+}$ to various coated ECM molecules on the microtiter wells (FIG. 1). The results indicated that there were weak interactions in the binding of recombinant decorin proteoglycan (vvHDCN) to collagen type I, II, IV, V, and VI (FIG. 1A). The binding of decorin to fibronectin was twice as strong in the presence of $Zn^{2+}$ ions compared to the absence of $Zn^{2+}$ (FIG. 1A). Strikingly, decorin could also bind to laminin and fibrinogen and both interactions were also enhanced in the presence of $Zn^{2+}$ ions (FIG. 1A). High non-specific binding backgrounds were observed with 1% BSA coated wells when using a common wash buffer containing 0.05% Tween-20. A high percentage of detergent (0.5% tween-20) was then used to decrease the non-specific binding background (data not shown). The binding interactions of recombinant intact decorin to collagens were decreased in the presence of the high percentage detergent (FIG. 1A). The interactions with laminin, fibronectin, and fibrinogen were not affected by the detergent in wash buffer.

Figure 1B:
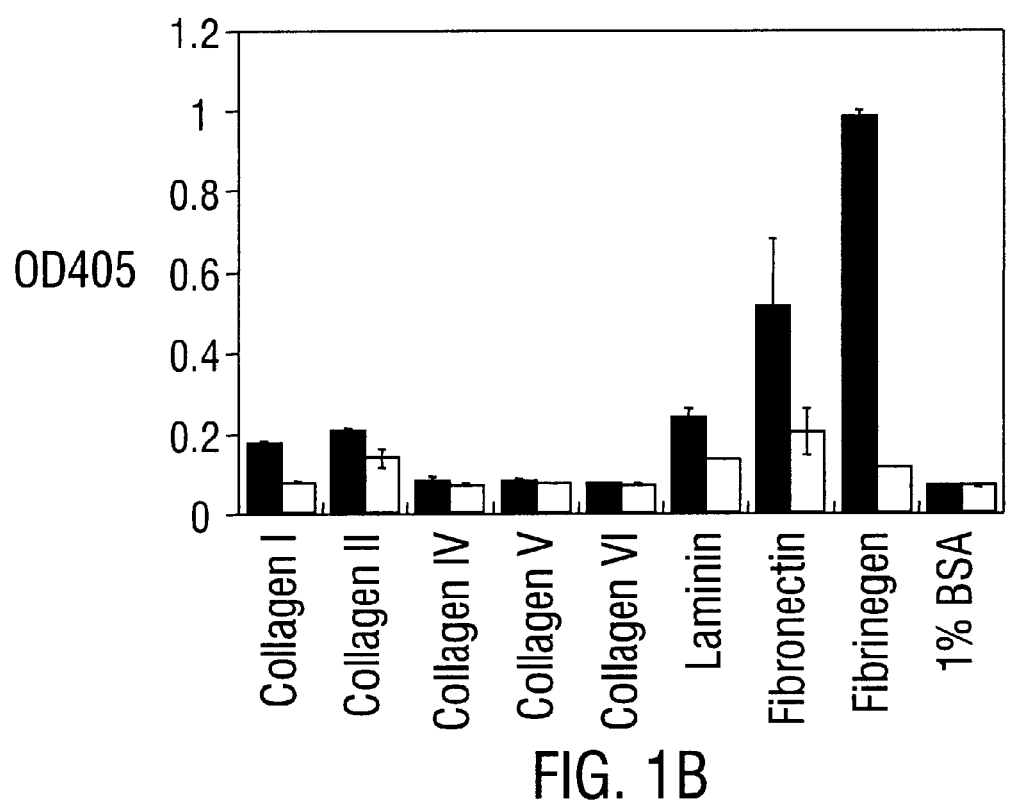

The Decorin N-terminal Domain Showed $Zn^{2+}$-dependent Binding Affinity to Fibrinogen The binding interaction of decorin N-terminus to the ECM molecules was compared in the presence and in the absence of $Zn^{2+}$ ions using biotin-labeled recombinant maltose binding protein-decorin N-terminal domain (MBP-MD4) fusion protein added to various ECM coated wells. The binding of decorin N-terminus (MBP-MD4) to fibrinogen is significantly $Zn^{2+}$ dependent (FIG. 1B). The biotin-labeled MBP-MD4 also showed binding activity to collagen I, II, laminin, fibronectin in the presence of $Zn^{2+}$ in high detergent wash buffer condition (FIG. 1B). The fusion protein carrier, MBP, by itself, did not show binding activity to any of the tested ECM molecules (data not shown). Additionally, avidin-alkaline phosphatase which was used to detect the biotin-labeled decorin did not bind to any tested ECM molecules (data not shown).

In the binding assays, the interaction of decorin to collagen was sensitive to detergent. The binding activity of decorin proteoglycan (vvHDCN) to coated collagens was weak in low detergent buffer, and decreased to non-detectable levels using high detergent wash buffer, suggesting a type of hydrophobic interaction. In contrast, there was no affect on the interaction of decorin to laminin, fibronectin, and fibrinogen in the low or high percentage of detergent in wash buffer. The binding activity of intact decorin or decorin N-terminal domain to laminin, is shown in FIGS. 1A and B.

The Specificity of Decorin Core Protein Binding to Fibrinogen

Figure 2:
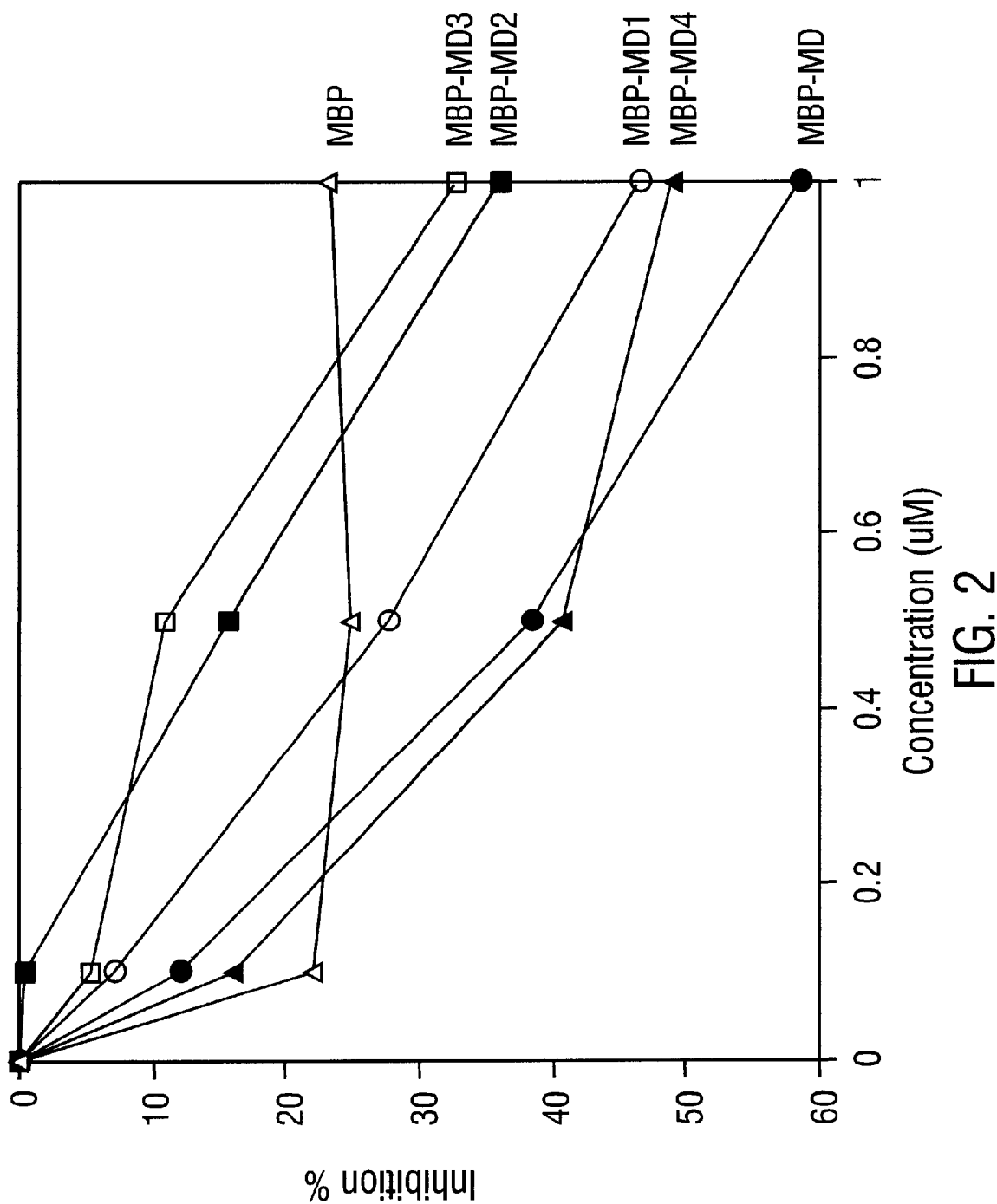
FIG. 2 Specificity of decorin core protein fragments binding to fibrinogen. Various recombinant decorin core protein fragments made as maltose binding protein fusions were tested for their ability to compete with biotin-labeled recombinant full length decorin (MBP-MD) for binding to fibrinogen in solid phase binding assays in the presence of 5 mM $ZnCl_2$ and 1 mM EDTA. MBP-MD (black circle) contains decorin full length core protein, MBP-MD1 (clear circle) contains decorin N-terminus and the LRR region, MBP-MD2 (black square) contains the LRR region, MBP-MD3 (clear square) contains LRR region and C-terminus, MBP-MD4 (black triangle) contains decorin N-terminus only, and MBP (clear triangle) is the maltose binding protein as a negative control.

To localize the fibrinogen binding domain on decorin core protein, variant recombinant decorin core protein fragments were made as maltose binding protein (MBP) fusions and were used in competitive assays. The full length decorin core protein (MBP-MD), the core protein lacking C-terminal domain (MBP-MD1), and the decorin N-terminal domain (MBP-MD4), which all contain the decorin N-terminal domain were stronger inhibitors compared to the other constructs. MBP-MD2 contains LRRs and MBP-MD3 decorin core protein lacks N-terminal domain. The results indicate that the major fibrinogen binding site is located at N-terminal domain of decorin core protein (FIG. 2).

Characterization of the Interaction of Decorin N-terminal Domain to Fibrinogen

Figure 3A:
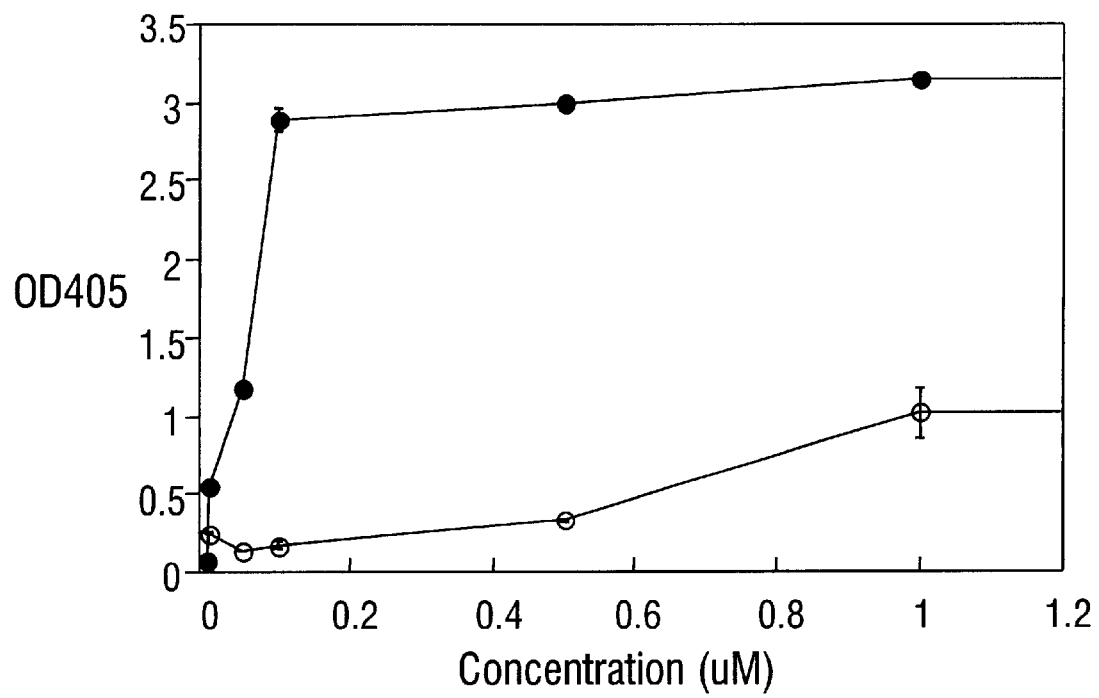
FIG. 3. Characterization of decorin binding to fibrinogen. Solid phase binding assays were used to characterize the binding activity of MBP-MD4 to fibrinogen. Binding of MBP-MD4 to fibrinogen is dose-dependent (A). Binding of MBP-MD4 to fibrinogen is time-dependent (B). Various divalent cations at 5 mM in the presence of 1 mM EDTA were used to test their affect on the binding of MBP-MD4 to fibrinogen (C). All the assays were done in the presence of 5 mM $ZnCl_2$ and 1 mM EDTA in (A) and (B). Back dots or bars represent the binding of MBP-MD4 to fibrinogen, clear dots or bars represent the binding of MBP to fibrinogen.

Decorin N-terminus (MBP-MD4) binds to fibrinogen only in the presence of $Zn^{2+}$ suggesting a three-molecule interaction. To further characterize this interaction, a series of solid phase binding assays in the presence of $Zn^{2+}$ ions were carried out. The binding of MBP-MD4 to fibrinogen was in a concentration-dependent manner. The binding interaction increased with the increasing concentration of fibrinogen until saturation, suggesting a specific interaction was occurred in the presence of $Zn^{2+}$ (FIG. 3A).

Figure 3B:
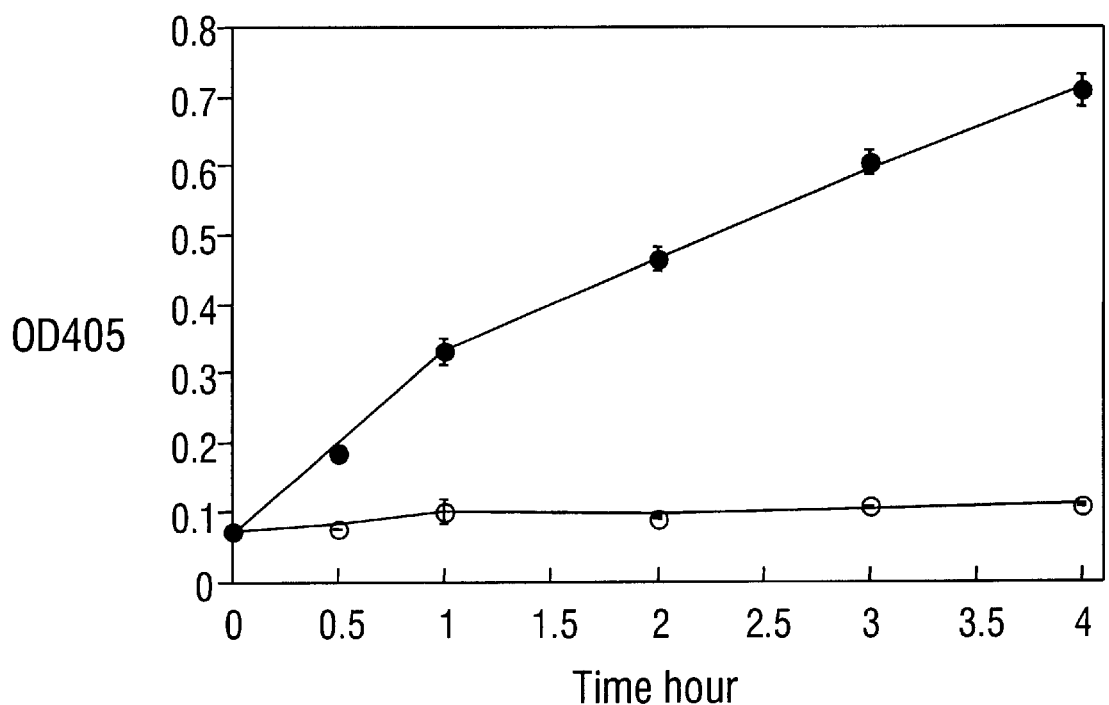

The binding of MBP-MD4 to fibrinogen was time-dependent (FIG. 3B). This unsaturable time curve binding was unusual suggesting that a slower cross-link reaction by intermolecule disulfide bonding between decorin molecules might occur.

Figure 3C:
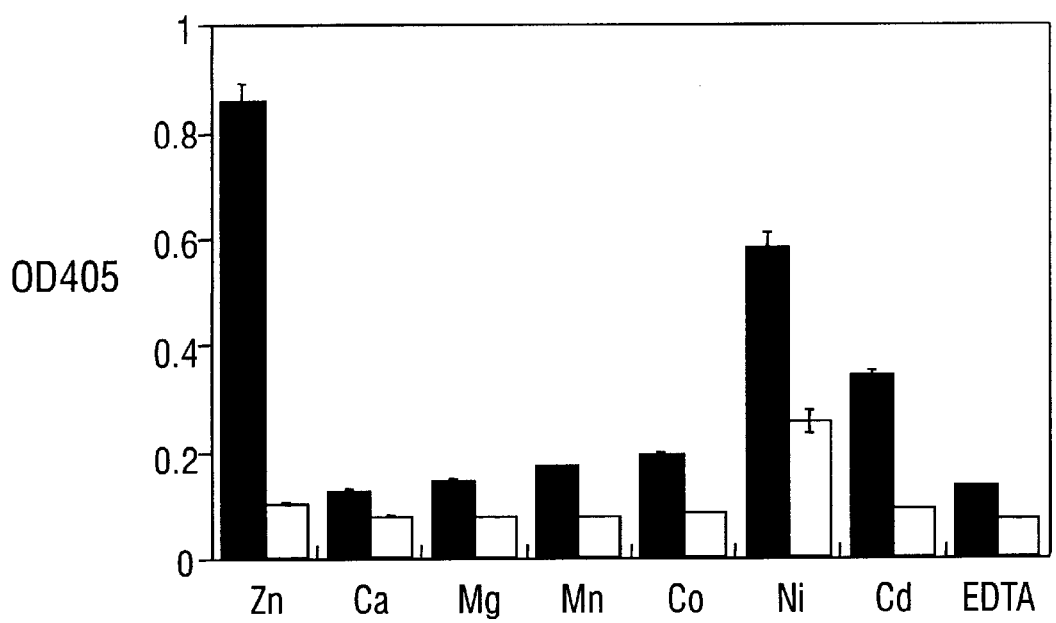

To investigate the ion specificity for the decorin-fibrinogen interaction, variant divalent cations were added into the binding assays. The enhancement affect was $Zn^{2+}$>$Ni^{2+}$>$Cd^{2+}$>$Co^{2+}$>$Mn^{2+}$, $Mg^{2+}$, $Ca^{2+}$ for the binding of MBP-MD4 to fibrinogen (FIG. 3C).

The binding Affinity of Decorin N-terminus to Fibrinogen

Figure 4:
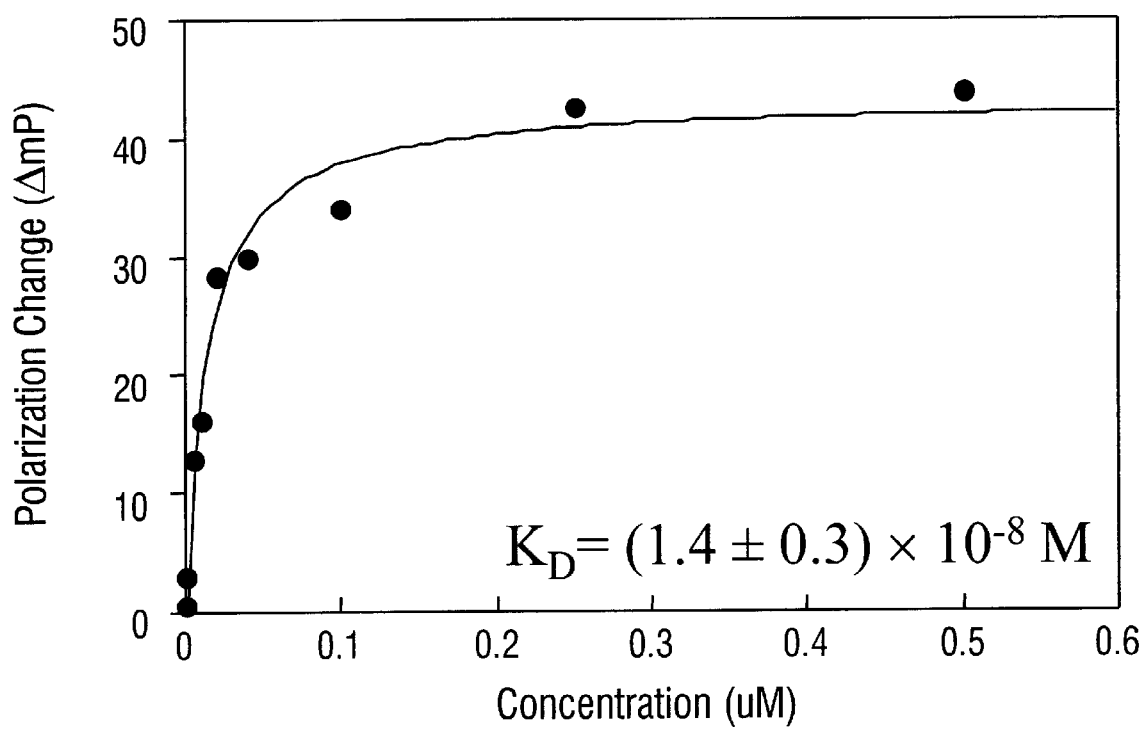
FIG. 4. Binding affinity of MD4 peptide to fibrinogen. Fluorescence polarization assays were used to measure the binding affinity of fluorescein labeled recombinant decorin N-terminal peptide (MD4) to fibrinogen. The binding curve represents the best fit from at least three experiments.

To measure the binding affinity of decorin N-terminus to fibrinogen, fluorescein labeled isolated decorin N-terminal peptide (MD4) was incubated with increasing concentrations of fibrinogen in the presence of 15 uM $ZnCl_2$. The dissociation constant of MD4 to $Zn^{2+}$ ions was 0.5 uM (Yang, 1999). A saturation plot was obtained with increasing concentration of fibrinogen versus the response of changed polarization (FIG. 4). The calculated apparent dissociation constant $K_D$ was $(1.4\pm0.3)\times10^{-8}$ M. In the absence of $Zn^{2+}$ by adding 1 mM EDTA, no interaction was observed (data not shown).

The Decorin N-terminus Bound to Fibrinogen α and β Chains

Figure 5:
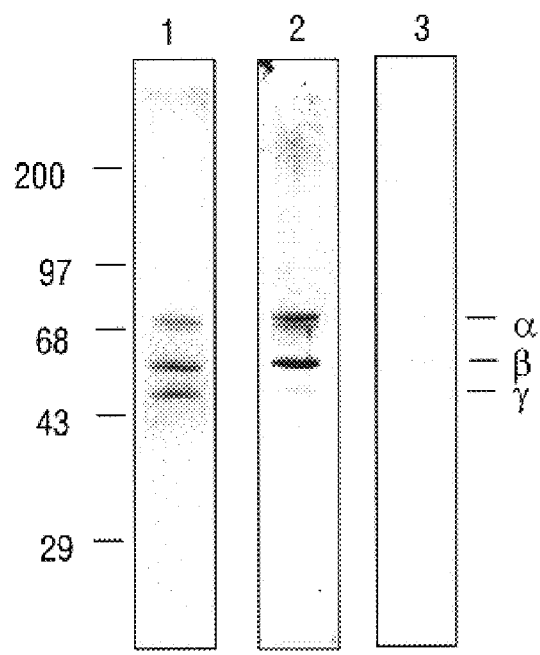
FIG. 5. MBP-MD4 binds to fibrinogen α and β chains. The decorin binding sites on fibrinogen polypeptide chains were localized by separating three fibrinogen chains on 10% SDS-PAGE and probed with biotin-labeled MBP-MD4. Lane 1 shows the commassie blue stained fibrinogen α, β, and γ chains, lane 2 indicates that α and β chain were blotted with MBP-MD4, and lane 3 indicates that MBP, by itself, does not bind to any of the fibrinogen polypeptides.

To localize the decorin N-terminus binding region in fibrinogen, Western ligand binding assay was employed. Three polypeptide chains of fibrinogen were separated by running a 10% SDS-PAGE, transferred to nitrocellulose membrane, and incubated with biotin-labeled MBP-MD4 or MBP. The fibrinogen polypeptide chains which bound with labeled decorin could then be detected by enzyme-linked streptavidin. The results indicated that MBP-MD4 bound to fibrinogen α and β chains and MBP, by itself, had no binding activity (FIG. 5).

Figure 6:
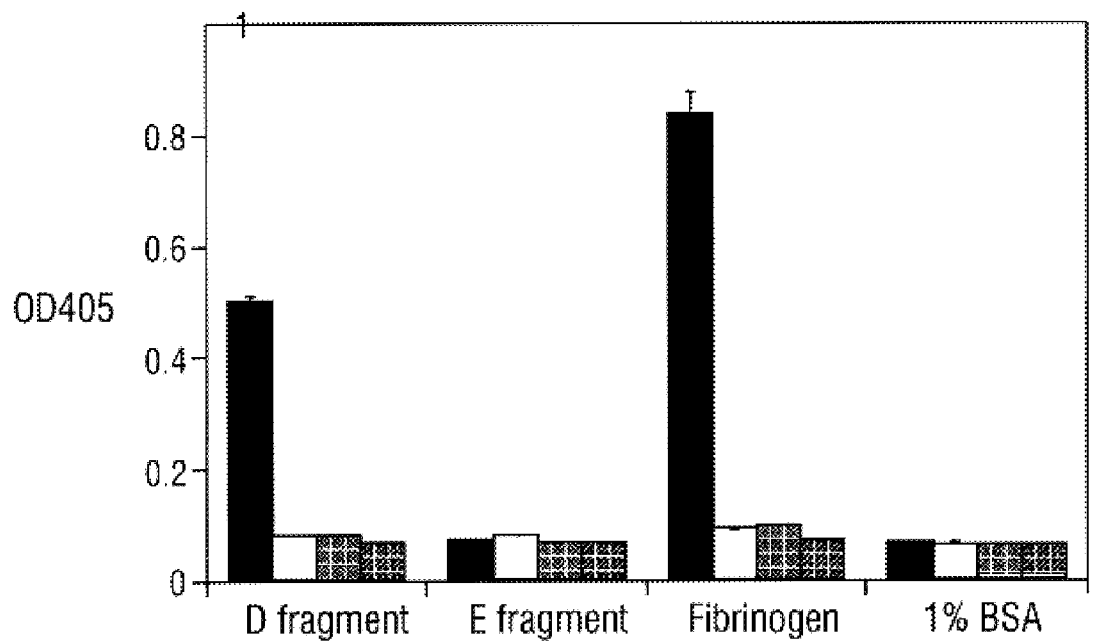
FIG. 6. $Zn^{2+}$-dependent binding of MBP-MD4 to fibrinogen D fragment. Solid phase binding assays shows that biotin-labeled MBP-MD4 also binds to fibrinogen D fragment and the interaction is $Zn^{2+}$-dependent. MMBP-MD4 does not bind to E fragments. The black bar indicates that the MBP-MD4 was incubated with 5 mM $ZnCl_2$ and 1 mM EDTA, clear bar indicates that the MBP-MD4 was incubated with 1 mM EDTA, a gray bar indicates that MBP was incubated with 5 mM $ZnCl_2$ and 1 mM EDTA, and-the hatched bar indicates MBP was incubated with 1 mM EDTA.

Decorin N-terminal Core Protein Bound to Fibrinogen D Fragment and the Interaction Was also $Zn^{2+}$-dependent Fibrinogen can be cleaved into parts as a central domain, E fragment and terminal, domains, and D fragments. To study the binding activity of decorin N-terminus to D and E fragments, biotin-labeled MBP-MD4 was incubated with purified D or E fragments coated on microtiter wells. The results showed that MBP-MD4 significantly bound to D fragments, not E fragments, and the interaction was also $Zn^{2+}$-dependent (FIG. 6).

The Specificity of Decorin N-terminal Core Protein to Fibrinogen D Fragments

Figure 7:
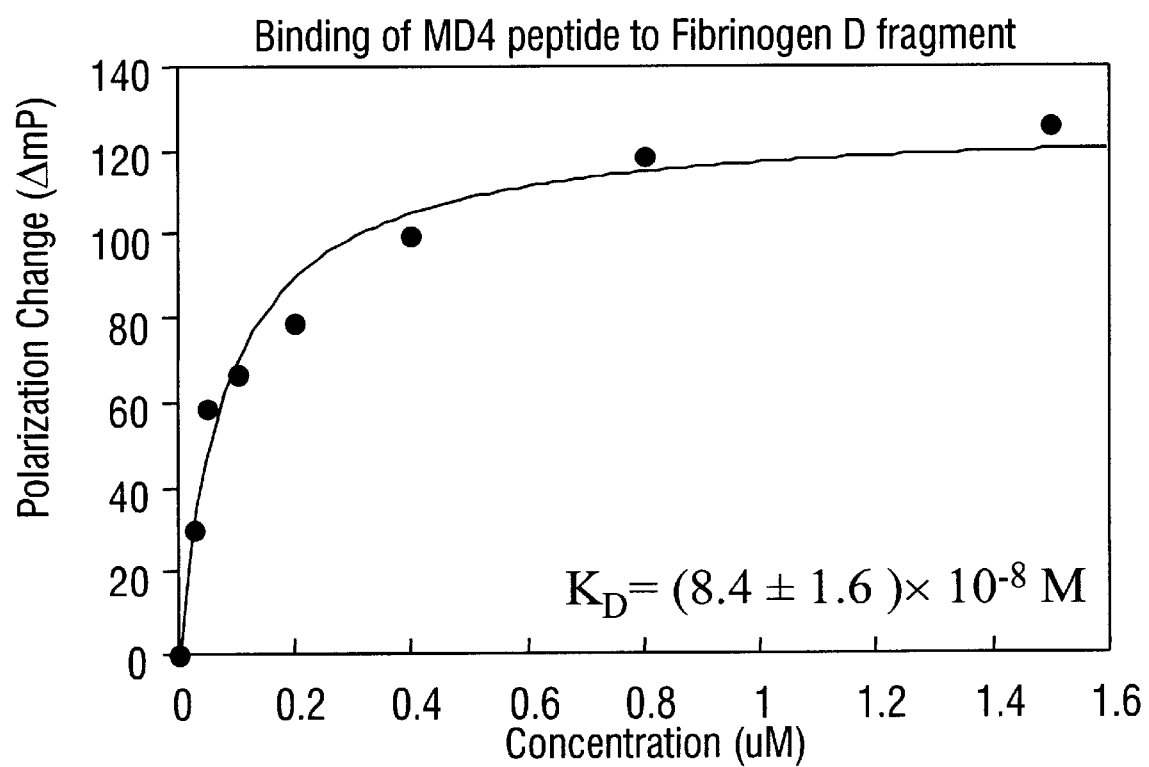
FIG. 7. Binding affinity of MD4 peptide to fibrinogen D fragments. Fluorescence polarization assays were used to measure the binding affinity of fluorescein labeled recombinant decorin N-terminal peptide (MD4) to fibrinogen D fragments. The binding curve represents the best fitting from at least three experiments.
Figure 8:
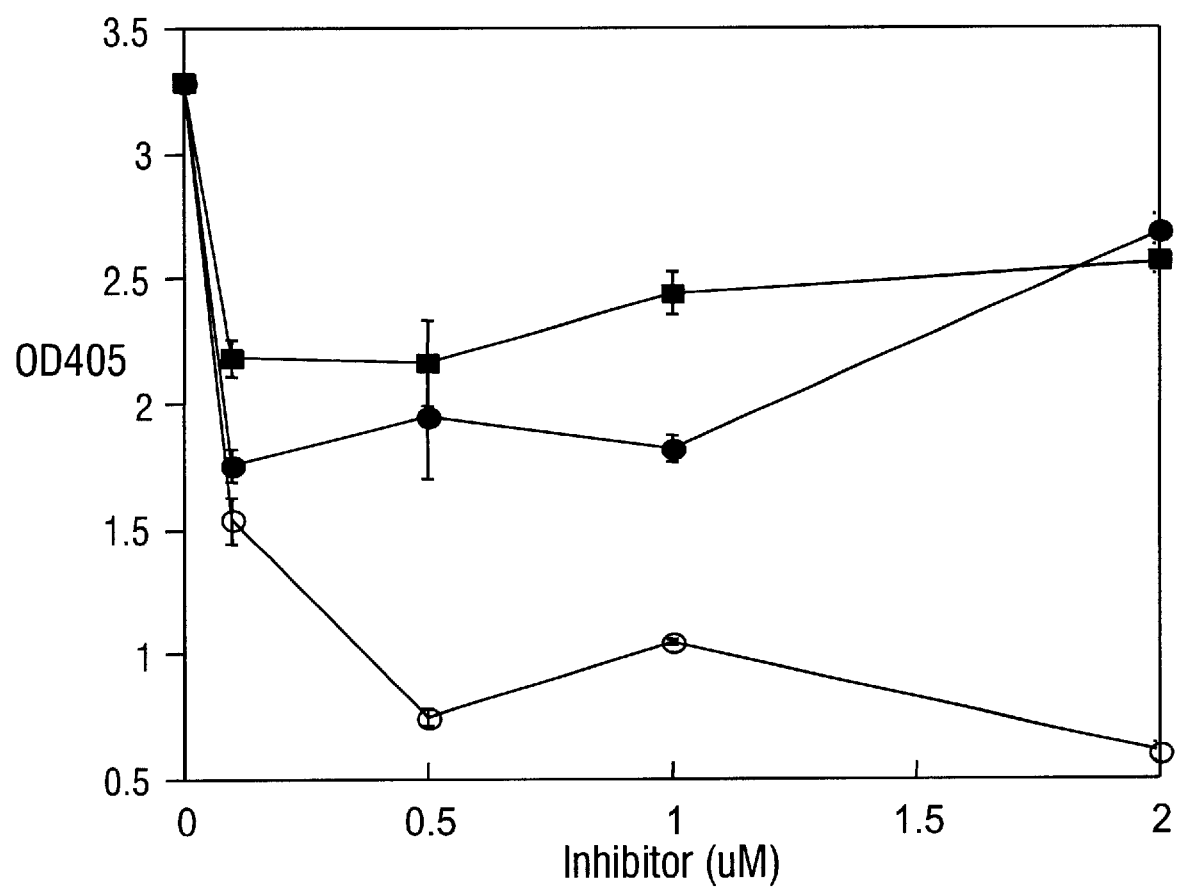
FIG. 8. Competitive binding of MD4 peptide in the interaction of MBP-MD4 to fibrinogen D fragments. The MD4 peptide (clear circle) is the strongest inhibitor of the binding of MBP-MD4 to D fragments compared to reduced and alkylated MD4 (black square) and G-P-R-P peptide (black circle).
Figure 9:
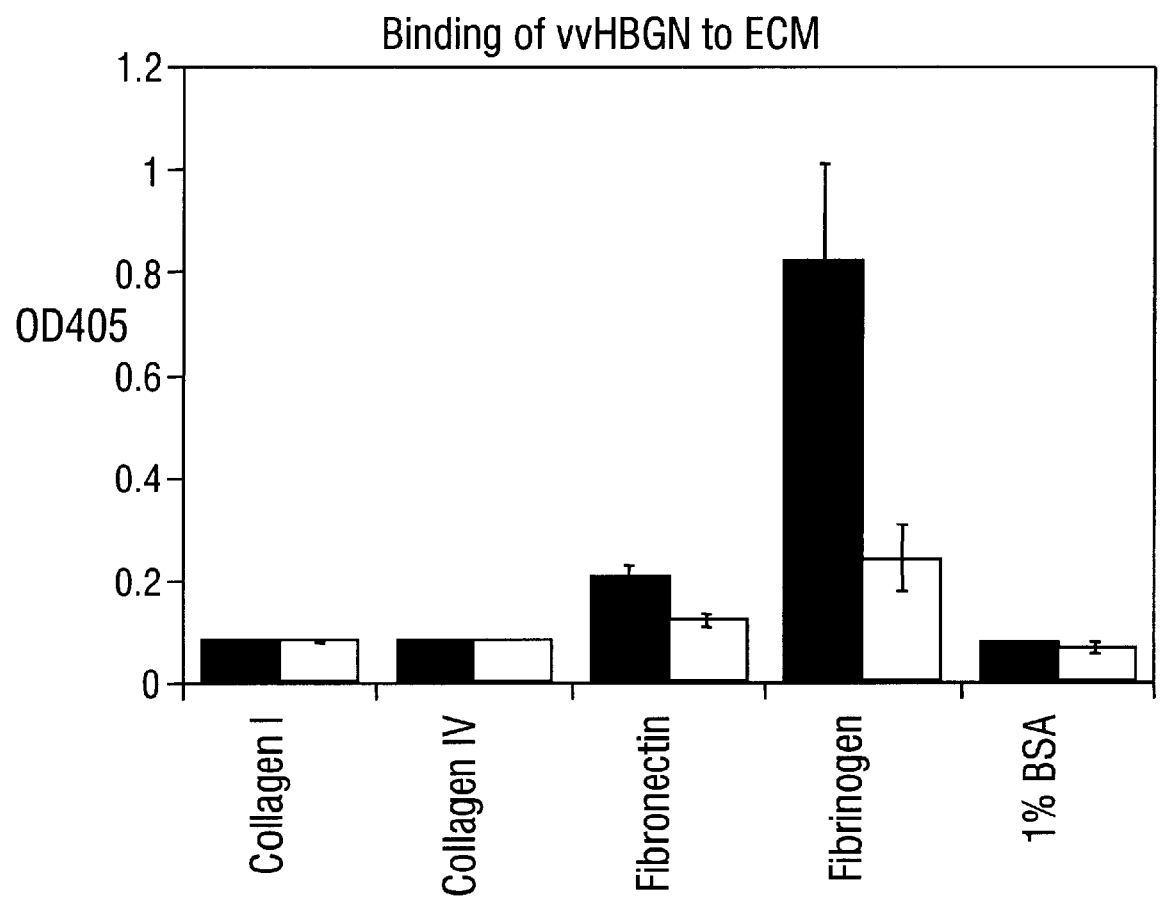
FIG. 9. Binding of biglycan to ECM molecules in the presence or absence of $Zn^{2+}$ ions. Biotin-labeled biglycan (vvHBGN), which was made as recombinant intact proteoglycan using a vaccinia virus based expression system in HT1080 cells and chemically labeled with biotin was examined for $Zn^{2+}$ dependent binding to different isolated ECM molecules coated in microtiter wells. The black bar indicates that the binding assays were done in the presence of 5 mM $ZnCl_2$ and 1 mM EDTA in the buffer (20 mM Tris-HCl, 500 mM NaCl, pH 7.5), the clear bar indicates that the binding assays were done in the presence of 1 mM EDTA in the buffer. A $Zn^{2+}$ dependent binding of biglycan to fibrinogen is demonstrated. Each data point represents the average of triplicated wells and the experiment has been repeated at least three times.

To measure the binding affinity of MD4 peptide to fibrinogen D fragments, fluorescence polarization experiments were carried out by incubating fluorescein labeled MD4 peptide with increasing concentration of fibrinogen D fragments and observing the change of polarization. The binding affinity of isolated MD4 peptide to fibrinogen D fragments in the presence of 15 uM $ZnCl_2$ was saturable and the apparent dissociation constant, $K_D$, was $(8.4\pm1.6)\times10^{-8}$ M (FIG. 7). Competitive binding to D fragment was compared for a four amino acid peptide, G-P-R-P which is known to bind to fibrinogen γ chain (Pratt, 1997) and to prevent fibrinogen from forming fibrin (Laudano, 1978; Laudano, 1980), reduced and alkylated MD4, unlabeled MD4 peptide, and MBP-MD4. The results showed that only MD4 peptide could compete with MBP-MD4 in binding to D fragment. Neither G-P-R-P peptide, nor reduced and alkylated MD4 peptide could inhibit the binding interaction (FIG. 8). MD4 peptide binds to fibrinogen α and β chains in Western ligand binding assays whereas G-P-R-P peptide binds to the γ chain of fibrinogen, therefore, both peptides bound to different sites in D fragment.

Additionally, the reported binding affinity $K_D$ of G-P-R-P peptide to fibrinogen D fragment is $1.7 \times 10^{-5}$ M (Laudano, 1978), which is weaker than the $K_D$ of MD4 peptide to D fragment (($8.4 \pm 1.6) \times 10^{-8}$ M) reported here (FIG. 7). That the reduced alkylated MD4 peptide which lost the $Zn^{2+}$ binding activity couldn't block the binding of MBP-MD4 to the D fragment fibrinogen suggested that $Zn^{2+}$ was required for the interaction of decorin N-terminus to fibrinogen.

The MD4 Peptide Inhibits Fibrin Clot Formation

A four amino acid long peptide, G-P-R-P, binds to the γ chain of fibrinogen D fragment and prolongs the clotting time in a closed system containing fibrinogen and thrombin (Laudano, 1978; Laudano, 1980). To demonstrate the affect of MD4 peptide in the clot formation, the clotting time was measured in the presence of MD4 peptide with fibrinogen and thrombin in physiological buffer (containing 15 uM of $ZnCl_2$). The results showed that MD4 peptide was a strong inhibitor in fibrin clot formation. The large gel like clot could not be formed in the presence of 100 uM MD4 peptide compared to the same amount of G-P-R-P peptide which could only delay the clot formation for 10 minutes (Table 1). The reduced alkylated MD4 peptide lost the inhibition activity in fibrin clot formation suggesting that loss of $Zn^{2+}$ binding activity by reduction and alkylation resulted in loss of fibrinogen binding activity.

TABLE 1

Comparison of Inhibition Effect in the Clotting Time of Peptides

| Peptide | Human Fibrinogen/Bovine Thrombin Clotting Time (min)[a] |
|---|---|
| MD4 | >200 |
| G-P-R-P | 10 |
| Alkylated MD4 | 5 |
| 1 mM EDTA | 12 |
| control | 5 |

[a]All peptides at final concentration of 0.1 mM with 1 mg/ml fibrinogen and 1 unit/ml thrombin in 20 mM Tris, 150 mM NaCl, 15 µM $ZnCl_2$, pH = 7.4.

REFERENCES

The following references, to the extent that they provide exemplary procedural or other details supplementary to those set forth herein, are specifically incorporated herein by reference.

Andrew, M., Mitchell, L., Berry, L., Paes, B., Delorme, M., Ofosu, F., Burrows, R., and Khambalia, B. (1992) J. Clin. Invest. 89, 321–326.

Bidanset, D. J., Guidry, C., Rosenberg, L. C., Choi, H. U., Timpl, R., and Haak, M. (1992) J. Biol. Chem. 267, 5250–5267.

Bidanset, D. J., Lebaron, R., Rosenberg, L., Murphy-Ullrich, J. E., and Hook, M. (1992) J. Cell Biol. 118, 1523–1531.

Brister, S. J., Ofosu, F. A., Heigenhauser, G. J., Gianese, F., and Buchanan, M. R. (1994) Thromb. Haemost. 71(4), 468–473.

Brown, D. C., and Vogel, K. G. (1989) Matrix 9, 468–478.

Danielson, K. G., Baribault, H., Holmes, D. F., Graham, H., Kadler, K. E., and Iozzo, R. V. (1997) J. Cell Biol. 136, 729–743.

Delorme, M. A., Xu, L., Berry, L., Mitchell, L., and Andrew, M. (1998) Thromb. Res. 90, 147–153.

Evanko, S. P., Raines, E. W., Ross, R., Gold, L. I., and Wight, T. N. (1998) Am. J. Pathol. 152, 533–546.

Everse, S. J., Spraggon, G., Veerapandian, L., Riley, M., and Doolittle, R. F. (1998) Biochemistry 37, 8637–8642.

Font, B., Aubert-Foucher, E., Goldschmidt, D., Eichenberger, D., and van der Rest, M. (1993) J. Biol. Chem. 268, 15015–25018.

Font, B., Eichenberger, D., Rosenberg, L. M., and van der Rest, M. (1996) Matrix Biol. 15(5), 341–8.

Hedbom, E. and Heinegård, D. (1993) J. Biol. Chem. 268, 27307–27312.

Hildebrand, A. Romaris, M., Rasmussen, L. M., Heinegård, D., Twardzik, D. R., Border, W. A., and Ruoslahti, E. (1994) Biochem. J. 302, 527–534.

Hocking, A. M., Strugnell, R. A., Ramamurthy, P., and McQuillan, D. J. (1996) J. Biol. Chem. 271, 19571–19577.

Lozzo, R. V., and Murdoch, A. D. (1996) FASEB 10, 598–614.

Klezovitch, O., Edelstein, C., Zhu, L., and Scanu, A. M. (1998) J. Biol. Chem. 273, 23856–23865.

Kresse, H., Liszio, C., Schönherr, E., and Fisher, L. W. (1997) J. Biol. Chem. 272, 18404–18410.

Krumdieck, R., Hook, M., Rosenberg, L., and Volanakis, J. E. (1992) J. Immunol. 149, 3695–3701.

Kyriakides, T. R., Zhu, Y-H, Smith, L. T., Bain, S. D., Yang, Z., Lin, M. T., Danielson, K. G., Iozzo, R. V., LaMarca, M., McKinney, C. E., Ginns, E. I., and Bornstein, P. (1998) J. Cell Biol. 140, 419–430.

Lacoviello, L., D'Adamo, M. C., Pawlak, K., Polishchuck, R., Wollny, T., Buczko, W., Donati, M. B. (1996) Thromb. Haemost. 76(6), 1102–1107.

Laudano, A. P. and Doolittle, R. F. (1978) Proc. Natl. Acad. Sci. 75, 3085–3089.

Laudano, A. P. and Doolittle, R. F. (1980) 19, 1013–1019.

LeBoeuf, R. D., Gregg, R. R., Weigel, P. H., and Fuller, G. M. (1987) Biochemistry 26, 6052–6057.

Lewandowska, K., Choi, H. U., Rosenberg, L. C., Zardi, L., and Culp, L. A. (1987) J. Cell Biol. 105, 1443–1454.

Linhardt, R. J., Desai, U. R., Liu, J., Pervin, A., Hoppensteadt, D., and Fareed, J. (1994) Biochem. Pharmacol. 47(7), 1241–1252.

Maimone, M. M. and Tollefsen, D. M. (1990) J. Biol. Chem. 265, 18253–18271.

Marx, G. (1987) Biopolymers 26, 911–920.

Marx, G. and Eldor, A. (1985) Am. J. Hematol. 19, 151–159.

Marx, G., Hopmeier, P., and Gurfel, D. (1987) Thromb. Haemost. 57(1), 73–76.

Matthiasson, S. E., Lindblad, B., Stjernquist, U., and Bergqvist, D. (1995) Haemostasis 25(5), 203–211.

Moscatello, D. K. Santra, M., Mann, D. M., McQuillan, D. J., Wong, A. J., and Iozzo, R. V. (1998) J. Clin. Invest. 101, 406–412.

Patel, S., Santra, M., McQuillan, D. J., Iozzo, R. V., and Thomas, A. P. (1998) J. Biol. Chem. 273, 3121–3124.

Pogány, G. and Vogel, K. G. (1992) Biochem, Biophys. Res. Comm, 189, 165–172.

Pratt, K. P., Côté, H. C. F., Chung, D. W., Stenkamp, R. E., and Davie, E. W. (1997) Proc. Natl. Acad. Sci. 94, 7176–7181.

Rada, J. A., Cornuet, P. K., and Hassell, J. R. (1993) Exp. Eye Res. 56, 635–648.

Radhakrishnamurthy, B., Tracy, R. E., Dalferes Jr., E. R., and Berenson, G. S. (1998) Exp. Mol. Pathol. 65, 1–8.

Ramamurthy, P., Hocking, A. M., and McQuillan D. J. (1996) J. Biol. Chem. 271, 19578–19584.

Riessen, R., Isner, J. M., Blessing, E., Loushin, C., Nikol, S., and Wight, T. N. (1994) Am. J. Pathol. 144, 962–974.

Schmidt, G., Hausser, H., and Kresse, H. (1991) Biochem J. 280, 411–414.

Schmidt, G., Robenet, H., Harrach, B., Glossl, J., Nolte, V., Hormann, H., Richter, H., and Kresse, H. (1987) J. Cell Biol. 104, 1683–1691.

Schönherr, E., Hausser, H., Beavan, L., and Kresse, H. (1995) J. Biol. Chem. 270, 8877–8883.

Schönherr, E., Lügering, N., Stoll, R., Domschke, W., and Kresse, H. (1997) Scand. J. Gastroenterol 32, 785–790.

Spraggon, G., Everse, S. J., and Doolittle, R. F. (1997) Nature 389, 455–461.

Svensson, L., Heinegård, D., and Oldberg, A. (1995) J. Biol. Chem. 270, 20712–20716.

Tollefsen, D. M., Pestka, C. A., and Monafo, W. J. (1983) J. Biol. Chem. 258, 6713–6716.

Vogel K. G., Paulsson, M., and Heinegård, D. (1984) Biolchem. J. 223, 587–597.

Vuento, M. and Vaheri, A. (1979) Biochemical. J. 183, 331–337.

Weber, I. T., Harrison, R. W., and Iozzo, R. V. (1996) J. Biol. Chem. 271, 31767–31770.

Whinna, H. C., Choi, H. U., Rosenberg, L. C., and Church, F. C. (1993) J. Biol. Chem. 268, 3920–3924.

Yamaguchi, Y., Mann, D. M., and Ruoslahti, E. (1990) Nature 346,281–284.

Yang, V. W-C, LaBrenz, S. R., Rosenberg, L. C., McQuillan, D., and Höök, M. (1999) J. Biol. Chem. (in press).

What is claimed is:

1. A method of inhibiting fibrin clot formation, the method comprising contacting fibrinogen with an effective amount of a decorin protein selected from the group consisting of the full length core protein of decorin and an active fragment containing the N-terminus of decorin.

2. The method of claim 1 wherein said decorin protein is in the form of the full length core protein of decorin.

3. The method of claim 1 wherein said decorin protein is in the form of an active portion or fragment containing the N-terminus of decorin.

4. The method of claim 1, wherein said decorin protein is dispersed in a pharmaceutically-acceptable carrier.

5. The method of claim 1, wherein said fibrinogen is comprised within an animal.

6. The method of claim 1, wherein said decorin protein is attached to the surface of a medical device or polymeric biomaterial.

7. A method of inhibiting fibrinogen aggregation, comprising contacting fibrinogen with an effective amount of a decorin protein composition comprising a decorin protein selected from the group consisting of the full length core protein of decorin and an active fragment containing the N-terminus of decorin.

8. The method of claim 7, wherein said, decorin protein is in the form of the full length core protein of decorin.

9. The method of claim 7, wherein said decorin protein is in the form of an active portion or fragment containing the N-terminus of decorin.

10. The method of claim 7, wherein said decorin protein is dispersed in a pharmaceutically-acceptable carrier.

11. The method of claim 7, wherein said fibrinogen is comprised within an animal.

12. The method of claim 7, wherein said decorin protein is attached to the surface of a medical device or polymeric biomaterial.

13. A method of inhibiting fibrin clot formation in a blood sample, said method comprising contacting said blood sample with an effective amount of a decorin protein composition comprising a decorin protein selected from the group consisting of the full length core protein of decorin and an active fragment containing the N-terminus of decorin.

14. The method of claim 13, wherein said decorin protein is in the form of the full length core protein of decorin.

15. The method of claim 13, wherein said decorin protein is in the form of an active portion or fragment containing the N-terminus of decorin.

16. The method of claim 13, wherein said decorin protein is dispersed in a pharmaceutically-acceptable carrier.

17. The method of claim 13, wherein said fibrinogen is comprised within an animal.

18. The method of claim 13, wherein said decorin protein is attached to the surface of a medical device or polymeric biomaterial.

19. A method of inhibiting fibrin clot formation in an animal, comprising providing to an animal a decorin protein pharmaceutical composition comprising an effective amount of a decorin protein selected from the group consisting of the full length core protein of decorin and an active fragment containing the N-terminus of decorin.

20. The method of claim 19, wherein said decorin protein is in the form of the full length core protein of decorin.

21. The method of claim 19, wherein said decorin protein is in the form of an active portion or fragment containing the N-terminus of decorin.

22. The method of claim 19, wherein said decorin protein is dispersed in a pharmaceutically-acceptable carrier.

23. The method of claim 19, wherein said decorin protein is attached to the surface of a medical device or polymeric biomaterial.

* * * * *